(12) United States Patent
Washburn et al.

(10) Patent No.: US 7,698,142 B2
(45) Date of Patent: Apr. 13, 2010

(54) VOICE CONTROL OF A GENERIC INPUT DEVICE FOR AN ULTRASOUND SYSTEM

(75) Inventors: Michael Joseph Washburn, Brookfield, WI (US); Brooks Matthew Hawley, Milwaukee, WI (US); Scot David Prichard, Muskego, WI (US)

(73) Assignee: General Electric Company, Schenectady, NY (US)

( * ) Notice: Subject to any disclaimer, the term of this patent is extended or adjusted under 35 U.S.C. 154(b) by 1290 days.

(21) Appl. No.: 11/048,587

(22) Filed: Feb. 1, 2005

(65) Prior Publication Data
US 2005/0131700 A1    Jun. 16, 2005

Related U.S. Application Data

(63) Continuation-in-part of application No. 10/659,143, filed on Sep. 10, 2003, now Pat. No. 7,052,459.

(51) Int. Cl.
*G01L 21/00* (2006.01)
(52) U.S. Cl. ............... 704/275; 704/270; 704/270.1; 704/231; 704/251
(58) Field of Classification Search .......... 704/275, 704/270, 270.1, 231, 251
See application file for complete search history.

(56) References Cited

U.S. PATENT DOCUMENTS

| | | | | |
|---|---|---|---|---|
| 5,544,654 | A | 8/1996 | Murphy et al. | 600/443 |
| 5,774,841 | A * | 6/1998 | Salazar et al. | 704/225 |
| 5,853,367 | A * | 12/1998 | Chalek et al. | 600/437 |
| 6,674,879 | B1 * | 1/2004 | Weisman et al. | 382/128 |
| 6,760,890 | B2 * | 7/2004 | Makinen | 716/4 |

* cited by examiner

*Primary Examiner*—Qi Han
(74) *Attorney, Agent, or Firm*—McAndrews, Held & Malloy, Ltd.; Peter J. Vogel; Michael A. Dellapenna

(57) ABSTRACT

The present invention relates to a system and method for providing voice control of a system, an ultrasound system for example. One embodiment of the present invention relates to a method of forming a generic input device used in an ultrasound system and responsive to at least one voice command. In at least one embodiment, the method comprises forming at least one display in the generic input device, the display having at least one tab associated therewith. The method further comprises defining a grid layout on at least one display and associating at least one control of the ultrasound system with at least one of the tab and the grid layout. At least one voice command is associated with at least one of the tab and grid layout.

9 Claims, 13 Drawing Sheets

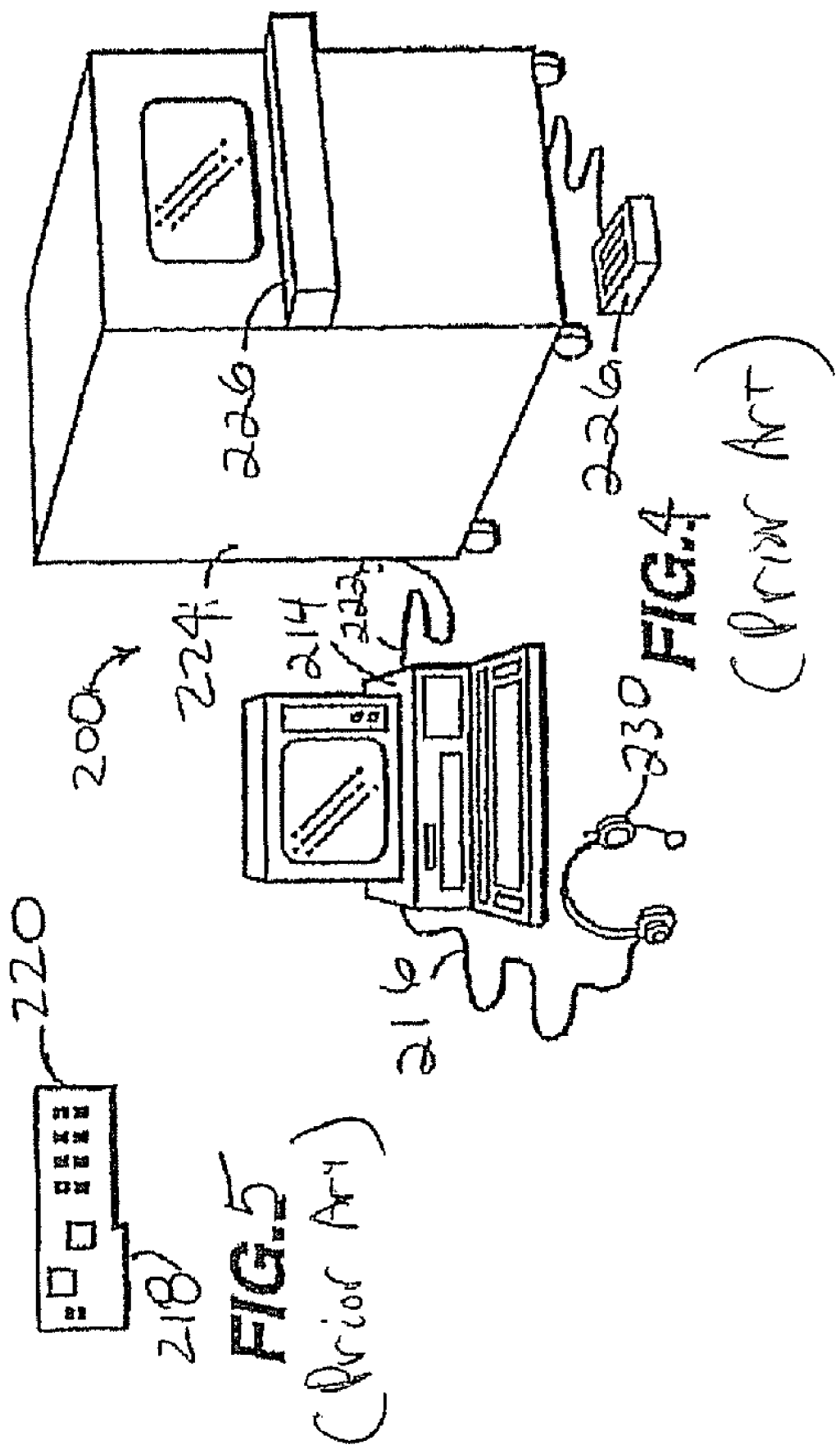

| | Mode 1 | Mode 2 | Mode 3 | Mode 4 | Mode 5 | ... | Mode Y |
|---|---|---|---|---|---|---|---|
| F1 | $a_1$ | $a_2$ | $a_3$ | $a_4$ | $a_5$ | ... | $a_y$ |
| F2 | $b_1$ | $b_2$ | $b_3$ | $b_4$ | $b_5$ | ... | $b_y$ |
| F3 | $c_1$ | $c_2$ | $c_3$ | $c_4$ | $c_5$ | ... | $c_y$ |
| F4 | $d_1$ | $d_2$ | $d_3$ | $d_4$ | $d_5$ | ... | $d_y$ |
| ⋮ | ⋮ | ⋮ | ⋮ | ⋮ | ⋮ | | ⋮ |
| FX | $z_1$ | $z_2$ | $z_3$ | $z_4$ | $z_5$ | ... | $z_y$ |

VOICE CONTROL OF A GENERIC INPUT DEVICE FOR AN ULTRASOUND SYSTEM

RELATED APPLICATIONS

This application is a continuation-in-part U.S. patent application Ser. No. 10/659,143 filed on Sep. 10, 2003 now U.S. Pat. No. 7,052,459, titled "Method and Apparatus For Controlling Ultrasound Systems", the complete subject matter of which is incorporated herein by reference in its entirety.

FEDERALLY SPONSORED RESEARCH OR DEVELOPMENT

Not Applicable

MICROFICHE/COPYRIGHT REFERENCE

Not Applicable

BACKGROUND OF THE INVENTION

This application is directed in general to control of ultrasound systems. This application is directed in particular to a voice control of a generic input device or user interface used with an ultrasound system and adapted to provide speech recognition without compromising control of the system.

It is contemplated that a number of situations may exist where, when using an ultrasound system, an operator (a doctor or sonographer for example) may have difficulty completing the exam using only the console. Some examples include upper and lower extremity exams, compression exams, carotid exams, neo-natal head exams, and portables. Working with large patients may further pose a problem to some smaller operators who can't physically reach both the console and the patient portion needed to be scanned. In addition, use of manual controls may lead to a repetitive stress disorder, causing the operator discomfort and decreasing their productivity.

Alternate methods exist for controlling the ultrasound system while away from the console (when the keyboard is insufficient or inconvenient for example). Some examples of such alternate methods include using a remote wand, a foot-switch, a second operator and limited voice control.

A remote wand coupled to the ultrasound machine enables an operator to conduct difficult exams. However, the remote wand does not enable the operator to complete an exam requiring the use of both hands (while supporting a patient's leg for example). A foot-switch attached to the ultrasound machine enables the operator to depress a small number of keys (typically two) by operating the switches with his or her feet. The keys on the foot-switch are generally defined as the most critical functions. This provides limited control of the ultrasound machine. However, the foot-switch solution is limited in several ways. Primarily, it does not provide broad control of the ultrasound machine. Generally a foot-switch only supports up to three commands. The operator must select which functions are to be controlled by the foot-switch based on their immediate needs. This is insufficient for most exams.

It is contemplated that an additional operator or assistant may assist with the examination, controlling the keyboard of the system in response to the doctor's or sonographer's spoken commands. It should be appreciated that having an additional operator assist in the examination may increase the cost of the examination. Further, there exists the possibility of miscommunication between the individual conducting the examination and the individual inputting information into the system.

It should be appreciated that one limitation associated with using voice commands to control an ultrasound system is communicating the command set to the operator. Leading ultrasound systems have hundreds of available commands. Memorizing all the hundreds of commands is difficult and may effect the speed of the recognition system. Furthermore, using a large set of commands, where a large portion of these commands are similar, may cause the commands to be misinterpreted. Such limitations, in conjunction with the variable accuracy in ultrasound systems, may lead to situations in which the user isn't sure if the lack of system response is due to an invalid command or the system's lack of understanding of the command.

A limited voice control system has been implemented which provides the operator with the ability to operate some of the keys of the keyboard using spoken commands. This voice control system recognizes a limited vocabulary of spoken commands. This vocabulary enables the operator to send a subset of the commands that may also be sent by the keyboard.

Still another system for voice control of an ultrasound machine is disclosed in U.S. Pat. No. 5,544,654. This voice control system limits the number of commands available to the user dependent on the state of the ultrasound system.

Known ultrasound systems have a large numbers of controls. Providing each system control using a unique voice command results in a very large command set. If each control is provided with a unique voice command, a very large command set size may result. This large command set may reduce the accuracy of the voice recognition system, slow the speed of command recognition, cause misinterpretations due to similarity of many of the commands and make it difficult for the operator to learn the full command list. In addition, if the system enables the operator to create controls once the system is installed, there may be no obvious way to drive the newly added or created control using predefined or existing voice commands.

BRIEF SUMMARY OF THE INVENTION

Embodiments of the present invention relates to natural voice commands used to simplify operations of a system (an ultrasound system for example). More specifically, embodiments of the present invention comprise a system and method adapted to provide simple and efficient operation of a device (an ultrasound machine for example) using at least one voice command. At least one embodiment of the ultrasound voice control system enables the user to complete an exam without using the console (i.e., the keyboard). This may be accomplished using a natural and flexible command grammar (i.e., structure) to control a generic input device or user interface, where the system controls are mapped to the generic input device or user interface. While a console control may only enable toggling the current state of a feature, it is contemplated that voice control in accordance with one embodiment of the present invention will provide for choosing toggling, enabling or disabling the state.

Embodiments of the present invention relate to a method of forming a generic input device or user interface adapted to control an ultrasound system and responsive to at least one voice command. In at least one embodiment, the method comprises forming at least one display in the generic input device or user interface, the display having at least one tab associated therewith. The method further comprises defining a grid layout on at least one display and associating at least one control of the ultrasound system with at least one of the tab and the grid layout. At least one voice command is associated with at least one of the tab and grid layout.

Yet other embodiments relate to a method for controlling an ultrasound system using a generic input device or user interface. This embodiment comprises receiving at least one spoken voice command and selecting at least one of a display, a grid label and an other control associated with the generic input device using at least one spoken voice command. The method further comprises controlling at least one feature of the ultrasound system based at least in part on the selected at least one display, grid label and other control.

Yet another embodiment relates to a voice-controlled ultrasound system. This embodiment comprises an ultrasound machine operating based on features and an input for receiving at least one generic voice command. The system further comprise a generic input or user interface having at least selectable element or control associated with the at least one generic voice command and a controller adapted to control at least one feature of the ultrasound machine based at least in part on the at least one generic voice command.

In another embodiment, a user interface for controlling an ultrasound system is provided. The user interface includes a plurality of selectable elements for controlling operation of the ultrasound system and a plurality of identifiers. Each identifier corresponds to one of the plurality of selectable elements and associates control commands with the selectable elements.

In still another embodiment, a method for controlling an ultrasound system is provided. The method includes associating a set of identifiers with a plurality of operations for controlling the ultrasound system, receiving control commands, and performing operations based upon the received control commands corresponding to one or more of the set of identifiers.

BRIEF DESCRIPTION OF SEVERAL VIEWS OF THE DRAWINGS

FIG. 4 is a perspective view of a voice activation system for controlling an ultrasound system in accordance with an exemplary embodiment of the present invention.

FIG. 5 is a an add-in card used with a voice activation system (similar to that illustrated in FIG. 4) in an ultrasound system in accordance with an exemplary embodiment of the present invention.

Figure 1:
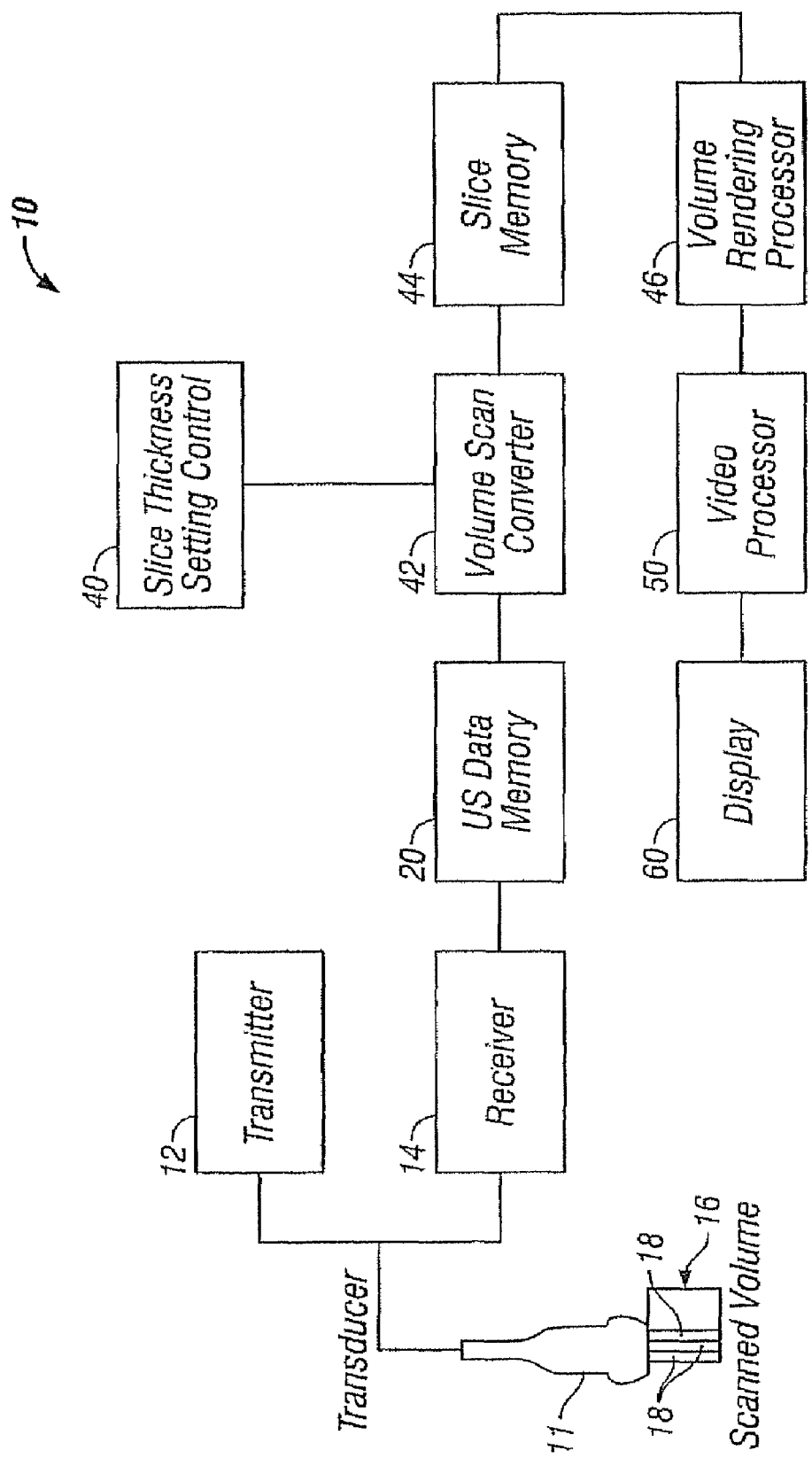
FIG. 1 is a block diagram of an ultrasound system in accordance with one exemplary embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an ultrasound system, machine, apparatus or device. However, it is understood that the present invention may be used with other devices or imaging systems.

As provided previously, generally ultrasound systems have a large set of controls the operator uses to drive the system behavior. Because the physical space on the system is limited, it may not be possible to expose all controls simultaneously. Known ultrasound systems use a touch panel, on-screen controls or other generic input devices to handle such limitation. The content of the generic input device typically varies depending on the context of the system, where only the necessary controls are exposed at any given time.

For example, the console control for Doppler mode may simply be a toggle button. However, the voice commands associated with the Doppler mode may include "Doppler" (to toggle), "Doppler On" (to enable), and "Doppler off" (to disable).

It is contemplated that, while many features of the ultrasound system may simply be enabled or disabled, other features (gain for example) are adjustable. That is, these features enable a user to select and or change a setting using a range of possible values (for example depth may range from 0 to 15). Voice control of these adjustable features may be accomplished by stating the command, a direction, and a value. Examples of such commands include changing gain (for example 2D, color, Doppler, etc.), depth, zoom, and baseline. Examples of direction may comprise positive and negative directions or values (and all synonyms). In one embodiment, if a direction is omitted, then a positive direction or value is assumed. The value represents a quantity to change the current value (or relative value for example) in the direction specified. If no value is specified, a default value (1 for example) is assumed, but a direction should be specified if no value is specified. It should also be appreciated that, while a default value of 1 is assumed, other default values may be used, including the same or differing default values selected or preset by the operator. It should also be understood that while the example command provided below are in English, other languages are contemplated.

Known ultrasound systems have large command set sizes to accommodate all such commands as provided previously. Such large command set sizes may reduce the accuracy and/or speed of the recognition system due to the size of the command set. Exemplary embodiments use generic controls, thereby avoiding associating unique voice commands for each control. In one or more embodiments, high use controls may have specific voice commands, but other less used controls may simply be driven by the generic voice commands. This reduces the size of the command set, increasing both accuracy and speed. Large command sets may result in misinterpreted commands due to the similarity of the voice commands. Embodiments using generic controls avoid have a unique voice command for each control. This reduction in command size, makes it possible to make each command in the command set sound unique. It is also contemplated that, to make the generic set of commands sound unique, letters or labels F, G, H and I are used rather than letters or labels A, B, C and D, which may make it difficult to distinguish a command such as "B1" from "D1" because they sound similar.

Exemplary embodiments comprise a system and method adapted to provide simple and efficient operation of a device (an ultrasound machine for example) using at least voice control. At least one embodiment of the ultrasound voice control system enables the user to complete an exam without using the console (the keyboard for example). This may be accomplished using a natural and flexible command grammar (i.e., structure) so that the operator's generic command controls the system. Commands in the present invention are short and concise; using language that is relevant to the user. While a console control may only enable toggling the current state of a feature, it is contemplated that voice control in accordance with at least one exemplary embodiment will enable choosing toggling, enabling or disabling the state.

Embodiments use a smaller command set, where less used commands may have generic voice controls. Operators do not need to learn voice commands for controls used infrequently but may instead use generic voice commands. Further, embodiments having a common user interface may be supported across a plurality of software versions that support voice command. This may eliminate or reduce training required for changes to the buttons, such as the addition of new buttons for new software features.

It is contemplated that the operator may want to add one or more controls, or reconfigure existing controls. Exemplary embodiments use a grid layout that are not specifically tied one control. That is, the system does not care what control is associated with a specific location in a grid. The system works whether it is a factory control or a user-specified control. It is contemplated that the generic controls may be directly labeled for further ease of use. Labels may be displayed only when voice command is active or based on user-preference to improve usability but minimize the impact on the operator who do not derive benefit from it.

FIG. 1 illustrates a block diagram of an exemplary embodiment of an ultrasound system 10. The ultrasound system 10 includes a probe 11, such as, for example, a transducer, connected to a transmitter 12 and a receiver 14. The probe 11 transmits ultrasonic pulses and receives echoes from structures inside a scanned ultrasound volume 16. A memory 20 stores ultrasound data from the receiver 14 derived from the scanned ultrasound volume 16. The volume 16 may be obtained by various techniques, including, for example, real-time imaging, volume scanning, scanning with transducers having positioning sensors, freehand scanning using a Voxel correlation technique or scanning with matrix array transducers and the like.

The probe 11 is moved, such as along a linear or arcuate path, while scanning a region of interest (ROI). At each linear or arcuate position, the probe 11 obtains scan planes 18. The scan planes 18 are collected for a thickness, such as from a group or set of adjacent scan planes 18. The scan planes 18 are stored in the memory 20, and then passed to a volume scan converter 42. In some embodiments, the probe 11 may obtain lines instead of the scan planes 18, and the memory 20 may store lines obtained by the probe 11 rather than the scan planes 18. The volume scan converter 42 may store lines obtained by the probe 11 rather than the scan planes 18. The volume scan converter 42 receives a slice thickness setting from a slice thickness setting control 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by the slice thickness setting control 40. The data slice is stored in slice memory 44 and is accessed by a volume rendering processor 46. The volume rendering processor 46 performs volume rendering upon the data slice. The output of the volume rendering processor 46 is passed to a video processor 50 and a display 60.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

It should be noted that the ultrasound system 10 may include additional or different components. For example, a user interface or input may be provided and used to control the operation of the ultrasound system 10, including, to control the input of patient data, scan parameters, a change of scan mode, and the like.

Figure 2:
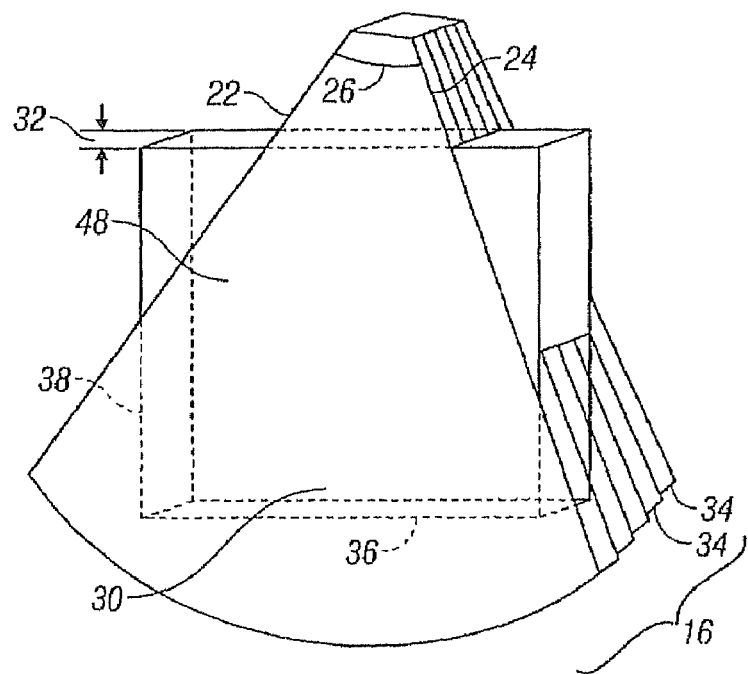
FIG. 2 is a perspective view of a real-time volume acquired by the system of FIG. 1 in accordance with an exemplary embodiment of the present invention.

FIG. 2 illustrates a real-time volume 16 acquired by the ultrasound system 10 of FIG. 1. It should be noted that the ultrasound system 100 of FIG. 3 as described below may also be used to acquire the real-time volume 16. The volume 16 includes a sector shaped cross-section with radial borders 22 and 24 diverging from one another at an angle 26. The probe 11 (shown in FIG. 1) electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the probe 11, and as illustrated in FIG. 1, are stored in the memory 20 and are scan converted from spherical to Cartesian coordinates by the volume scan converter 42. A volume comprising multiple scan planes is output from the volume scan converter 42 and stored in the slice memory 44 as a rendering box 30. The rendering box 30 in the slice memory 44 is formed from multiple adjacent image planes 34.

The rendering box 30 may be defined in size by an operator using a user interface or input to have a slice thickness 32, width 36 and height 38. The volume scan converter 42 may be controlled by the slice thickness setting control 40 to adjust the thickness parameter of the slice to form a rendering box 30 of the desired thickness. The rendering box 30 designates the portion of the scanned volume 16 that is volume rendered.

The volume rendering processor 46 accesses the slice memory 44 and renders along the slice thickness 32 of the rendering box 30.

Referring now to FIGS. 1 and 2, during operation, a slice having a pre-defined, substantially constant thickness (also referred to as the rendering box 30) is acquired by the slice thickness setting control 40 and is processed in the volume scan converter 42. The echo data representing the rendering box 30 may be stored in the slice memory 44. Predefined thicknesses between about 2 mm and about 20 mm are typical, however, thicknesses less than about 2 mm or greater than about 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image plane 34. Following processing in the volume rendering processor 46, the pixel data in the image portion 48 may pass through a video processor 50 and then to a display 60. The rendering box 30 may be located at any position and oriented at any direction within the scanned volume 16. In some situations, depending on the size of the region being scanned, it may be advantageous for the rendering box 30 to be only a small portion of the scanned volume 16.

Figure 3:
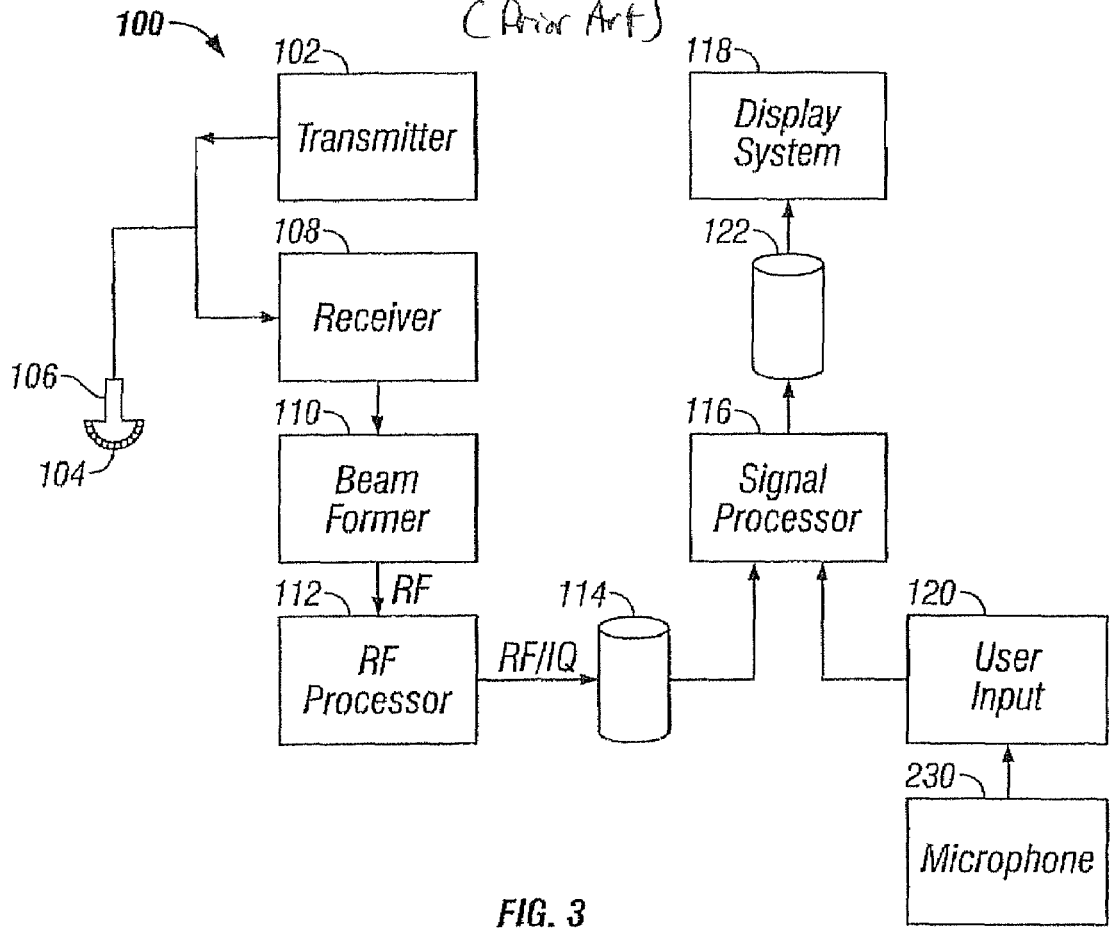
FIG. 3 is an ultrasound system in accordance with another exemplary embodiment of the present invention.

FIG. 3 illustrates a block diagram of another exemplary embodiment of an ultrasound system 100. The ultrasound system 100 includes a transmitter 102 that drives transducers 104 within a probe 106 to emit pulsed ultrasonic signals into a body. A variety of geometries may be used. The ultrasonic signals are back-scattered from structures in the body, like blood cells or muscular tissue, to produce echoes that return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage. A user input device 120 as described in more detail below may be used to control operation of the ultrasound system 100, including, to control the input of patient data, scan parameters, a change of scan mode, and the like. This may include using voice commands provided via a microphone 230.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information is displayed on the display system 118 at a slower frame-rate. An image buffer 122 is included for storing processed frames of acquired ultrasound information that are not scheduled to be displayed immediately. In an exemplary embodiment, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

In at least one embodiment, a host computer or PC 214 contains at least one control processor and hardware and software for providing voice control operation of an ultrasound system using a generic input device. FIG. 4 illustrates an ultrasound machine, device or apparatus, generally designated 200, having a voice activation system, for controlling the ultrasound machine (similar to that provided previously) in accordance with an exemplary embodiment of the present invention. In the illustrated embodiment, a microphone 230 is coupled to or communicating with a host computer 214 via connection 216. In at least one embodiment, host computer or PC 214 contains at least control processor and hardware and software for providing operation of the ultrasound system using voice control.

In one embodiment, the microphone 230 is a headset microphone. However, any microphone or other input device suitable for speech recognition applications (including, for example, lapel microphones, hand-held microphones, stand-mounted microphones, "far-talk" microphones, etc.) may be used. Additionally any mounting option may be used. It is contemplated that connection 216 connects the microphone 230 to the speech recognition hardware. In the illustrated implementation, a wired connection is illustrated. However, any microphone connection may be used, including, for example, wireless connections.

FIG. 5 illustrates connection 218 and speech recognition hardware/software 220 in accordance with at least one exemplary embodiment. In this embodiment, connection 218 connects the speech recognition system to host computer 214. In at least one embodiment, the speech recognition system is an add-in card, for example, interfacing using a PCI bus for example. However, other embodiments are contemplated, wherein the speech recognition system may be a separate module connected via a serial interface, or it may be designed to interface to the bus of another type of host computer. An embodiment further contemplates speech recognition software adapted to perform speech recognition. Any suitable commercial or custom speech recognition system may be used.

FIG. 4 further illustrates host computer 214 coupled to ultrasound device 224 via connection 222. In one embodiment, connection 222 comprises a wired connection, although other interfaces or connections are contemplated, including wireless connections. One exemplary embodiment comprises an embedded design, where the host computer is contained within the ultrasound system, connected to the computer bus of the ultrasound system for example. In this illustrated embodiment, the ultrasound device 224 includes a keyboard 226 and foot-switch 228.

Figures 6, 8:
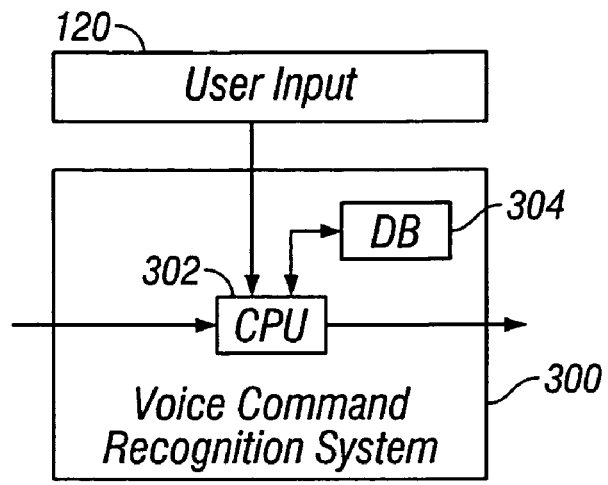
FIG. 6 is a block diagram of a voice command recognition system in accordance with an exemplary embodiment of the present invention.
FIG. 8 is a lookup table of the voice command recognition system of FIGS. 6 and 7 in accordance with an exemplary embodiment of the present invention.

The association of a voice command with a control command (represented by the icon 500 illustrated in FIGS. 9 and 10) for controlling an operation or parameter of the ultrasound systems 10, 100 and 200 is provided by a voice command recognition system. A block diagram of an exemplary embodiment of a voice command recognition system 300 is shown in FIG. 6. The voice command recognition system 300 includes a processor 302 (e.g., CPU) for receiving an audio signal, such as a voice command from a user, and processing the audio signal to determine the corresponding control command for use in controlling an operation or parameter of the ultrasound systems 10, 100 and 200. The processor 302 also receives information from the user input 120 (e.g., current mode of operation) and accesses a database 304 containing association information for associating a voice command with a control command. It should be noted that the voice command recognition system 300 may be provided separate from or as part of the user input 120 or user interface.

Figure 7:
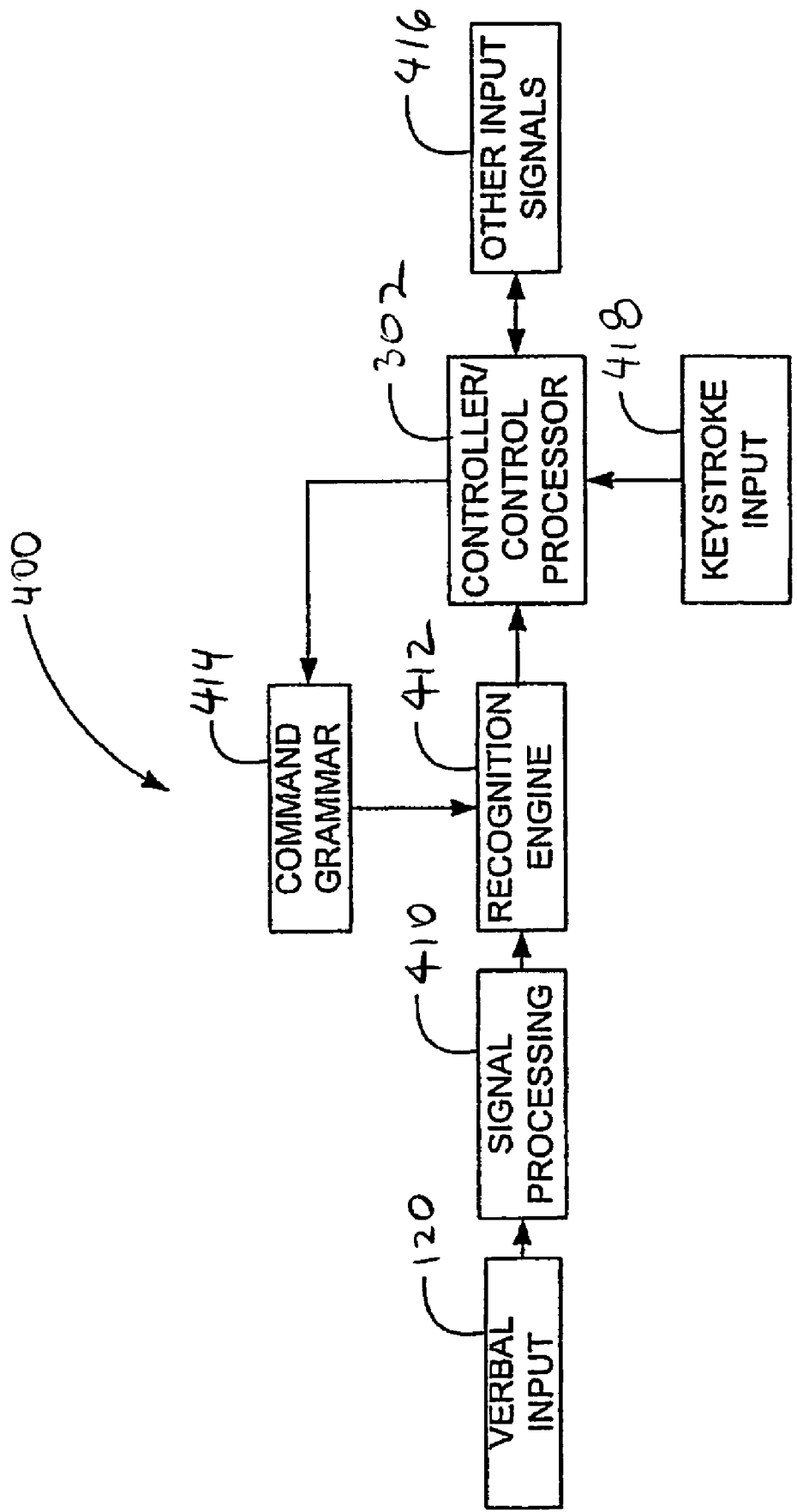
FIG. 7 is a block diagram of a voice command recognition system (similar to that illustrated in FIG. 6) in accordance with another exemplary embodiment of the present invention.

The database 304 contains one or more lookup tables 310 (Similar to that shown in FIG. 7). It should be noted that the database 304 having the lookup tables 310 contained therein may be stored, for example, in a memory or other storage component, for example, in local memory in the ultrasound systems 10, 100 and 200 or on a server remote from the ultrasound systems 10, 100 and 200. It should also be noted that the association information an may be provided in other forms, such as, for example, as lists in separate files stored within a memory.

FIG. 7 depicts a block diagram of another voice recognition system, generally designated 400, illustrating another exemplary embodiment of a voice control of an ultrasound machine or device similar to that described previously. In one embodiment, verbal input or voice commands 120 are entered into the system using an input device. Any suitable microphone or other input device is contemplated.

FIG. 7 further depicts verbal input 120 is translated or one or more signals derived from the verbal input (i.e., signal 1 processing 410). In one embodiment, this function may be implemented as part of the commercial speech recognition product.

Recognition engine 412 is shown communicating with signal processing 410 and command grammar 414. In one embodiment, this function may be part of the speech recognition product, including hardware and software. Recognition engine 412 compares the incoming speech to the vocabulary or command grammar 414 to determine if the spoken word matches any of the defined commands.

FIG. 7 further illustrates command grammar 414 communicating with recognition engine 412 and controller/control processor 302. In one embodiment, the command grammar 414 contains the reference commands (which in one embodiment may include look up table 310) that may be issued by the operator. In at least one embodiment, the total command grammar 414 may be subdivided into groups, or sub-vocabularies, each of which may be selected or deselected as part of the command grammar. It is contemplated that this function is also part of the speech recognition product, but may be customized to a particular application. The command structure and sub-vocabularies may be stored on disk or in the controller/control processor 302. Similar resources for the creation and management of vocabularies exist for the other commercial speech recognition products.

In at least one exemplary embodiment, the system or device includes an ultrasound system controller or control processor 302 (similar to that provided previously). In at least this embodiment, the controller/control processor 302 communicates with at least the recognition engine 412 and the command grammar 414 and is the software/hardware module that controls the overall ultrasound system or device.

It is further contemplated that, in addition to be controlled using verbal controls, at least one embodiment may be controlled using keystroke inputs or other input signals 418 and 416 respectively. FIG. 7 contemplates that an ultrasound system keyboard and/or other input devices (for example a mouse, rollerball, footswitch, image-capture device, touch panel, a wireless remote wand, other wireless devices) are adapted to produce and transmit one or more inputs or signals to the controller/control processor 302.

Referring now to a user interface or input, such as, for example, the user input device 120 (shown in FIG. 3), various embodiments may be implemented for controlling the ultrasound systems 10, 100 and 200. Such various embodiments may include control functionality, such as a set of user controls for controlling the ultrasound systems 10, 100 and 200. The set of user controls may be provided, for example, as part of a touch screen or panel, or as manual inputs, including, for example, user operable switches, buttons, and the like. The set of user controls may be manually operable or voice operated.

Figure 9:
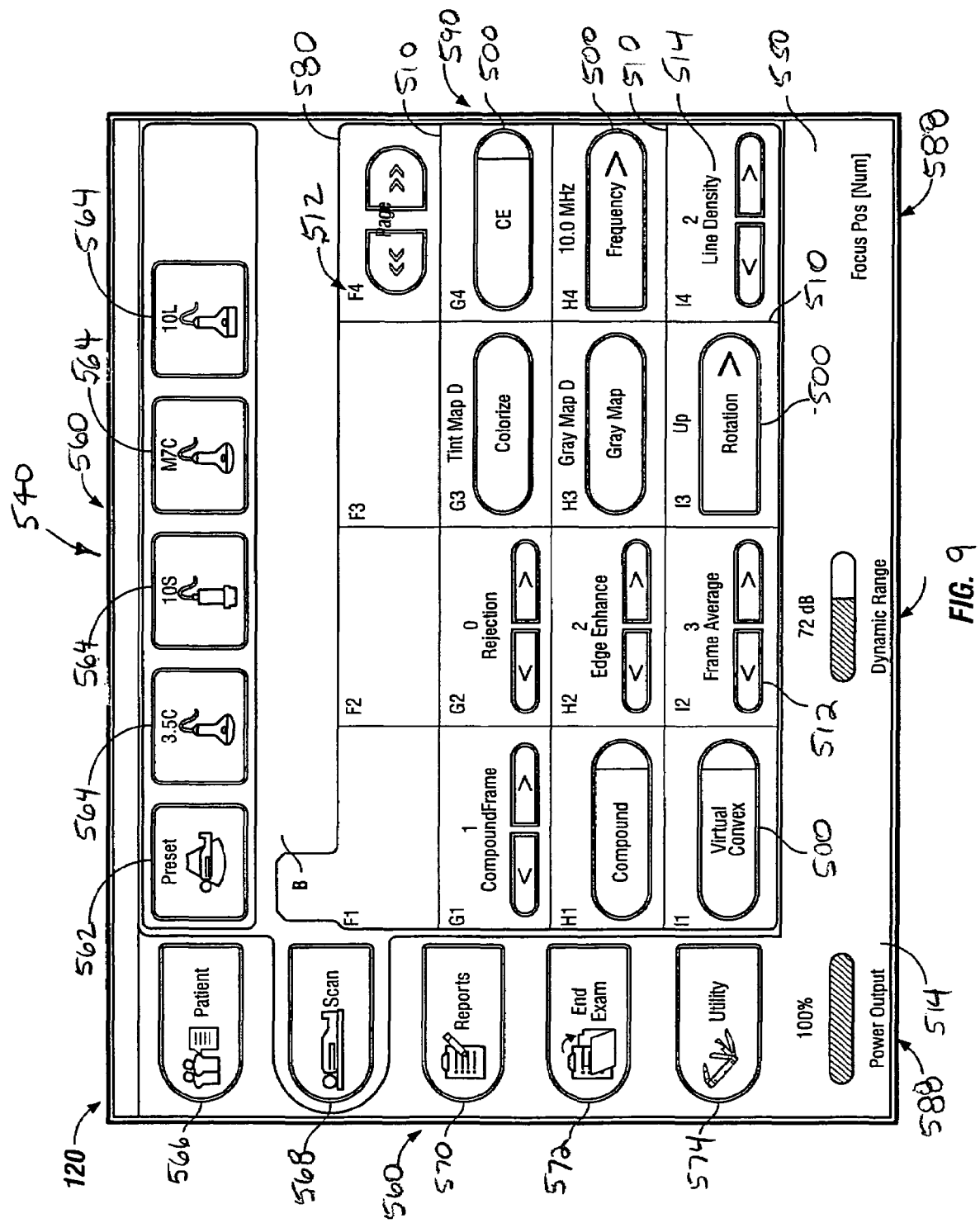
FIG. 9 is an exemplary embodiment of a user input of an ultrasound system displaying an exemplary control screen.

As shown in FIG. 8, an exemplary embodiment of a lookup table 310 includes a first column 320, which includes the possible identifiers (e.g., identifiers 512 in FIG. 9) for one set or row of the matrix in the control portion (e.g., F1 through F4 identified as 580 in FIG. 9). A plurality of mode columns 322 corresponding to the different modes of operation of the ultrasound systems 10, 100 and 200 are provided and include address values corresponding to control commands for each of the modes of operation. Thus, for each identifier entry in the first column 320, a corresponding row includes addresses (e.g., $a_1$ to $a_5$ for five different modes of operation) in the database 304 for the control commands associated with the identifier (identified 512 in FIG. 9) for each mode of operation. In one exemplary embodiment, the length of the columns and rows is determined based upon the number of identifiers and modes of operation for the ultrasound systems 10, 100 and 200, respectively. It should be noted that separate lookup tables 310 may be provided for each set of identifiers or a single lookup table 310 may be provided for all possible identifiers. Additionally, the first column 320 may be modified to include word commands or physical control inputs with the corresponding row entries identifying the addresses in the database 304 for the operations to be performed associated with the word commands or physical control inputs, respectively.

In an exemplary embodiment as shown in FIG. 9, a user input device 120 may include a user interface, such as, for example, a panel or screen 550, that is operable and selectable by touching the screen 550 (i.e., a touch panel) to select the desired operation or command for controlling the ultrasound systems 10, 100 and 200. The user input device 120 may also include a voice control input or voice activated component (not shown), such as a microphone 230 (shown in FIGS. 3 and 4), for controlling the operation of the ultrasound systems 10, 100 and 200.

In this embodiment, panel or screen 550 comprises at least one control provided on one or more tabs, each tab containing at least one grid layout. In at least one embodiment, such control (Tab 1 for example) may be used to select a particular tab and display, and a designator or grid label (for example "I4") may be used to drive a particular control within the grid layout.

Specifically, and as shown in FIG. 9, the screen 550 includes a first set of selectable elements 560, for example, a plurality of icons selectable by a user touching the icons on the screen 550 or by voice command as described below, that control operation of the ultrasound systems 10, 100 and 200 in various modes of operation. In one exemplary embodiment, the plurality of selectable elements 560 are fixed and do not change based upon the particular mode of operation. Thus, the icons do not change when the mode of operation changes, for example, as selected by a user. The first set of selectable elements 560 may include, for example, functionality to control general operation of the ultrasound systems 10, 100 and 200 (alternatively referred to as other control portion 530). The other control portion 530 may control, for example, the area of a patient to scan (Preset icon 562) and/or the selection of a particular transducer to use for a scan (3.5C, 10S, M7C and 10L icons 564). The other control portion 530 may also allow for selection of general operations such as to enter patient information (Patient icon 566), start a scan (Scan icon 568), create or generate a report (Reports icon 570), end a scan or exam (End Exam icon 572) and/or configure the ultrasound machines 10, 100 and 200 (Utility icon 574). These icons are selectable by touching the screen 550 or by voice commands as described below.

The screen 550 also includes a control portion 580 having a second set of selectable elements 590, for example, a plurality of icons 500 selectable by a user touching the icons 500 on the screen 550 or by voice command as described below, that control operation of the ultrasound systems 10, 100 and 200 in various modes of operation. In one exemplary embodiment, the plurality of selectable elements 590 change based upon the selected mode of operation. Thus, the icons 500 change when the mode of operation changes, for example, as selected by a user. A mode selection element, such as a tab 582, indicates the current mode of operation and defines a set of icons 500 corresponding to that mode of operation to be displayed in the control portion 580. The second set of selectable elements 590 may include, for example, functionality to control operation of the ultrasound systems 10, 100 and 200 in the selected mode of operation. The icons 500 may control, for example, the parameters of operation during the selected mode of operation. For example, and as shown in FIG. 9, when a B-mode of operation is selected, the icons 500, may control, for example, the scanning parameters in the B-mode, such as compounding, rotation, map, frequency, etc. These icons 500 are selectable by touching the screen 550 or by voice commands as described below.

As illustrated in FIG. 9, the voice command "H1" for example would turn on/off the Compound feature, while the command "H3" for example would turn on/off the Gray Map feature. The voice command "I4" or "I4 Up" for example, would increase the Line Density setting by 1 step, the voice command "H2 down" for example would decrease the Edge Enhance by 1. Examples are provided in Table 1 below. It should be appreciated that different grid layouts would have similar grid labels, but would be associated with different controls as provided below.

Figure 10:
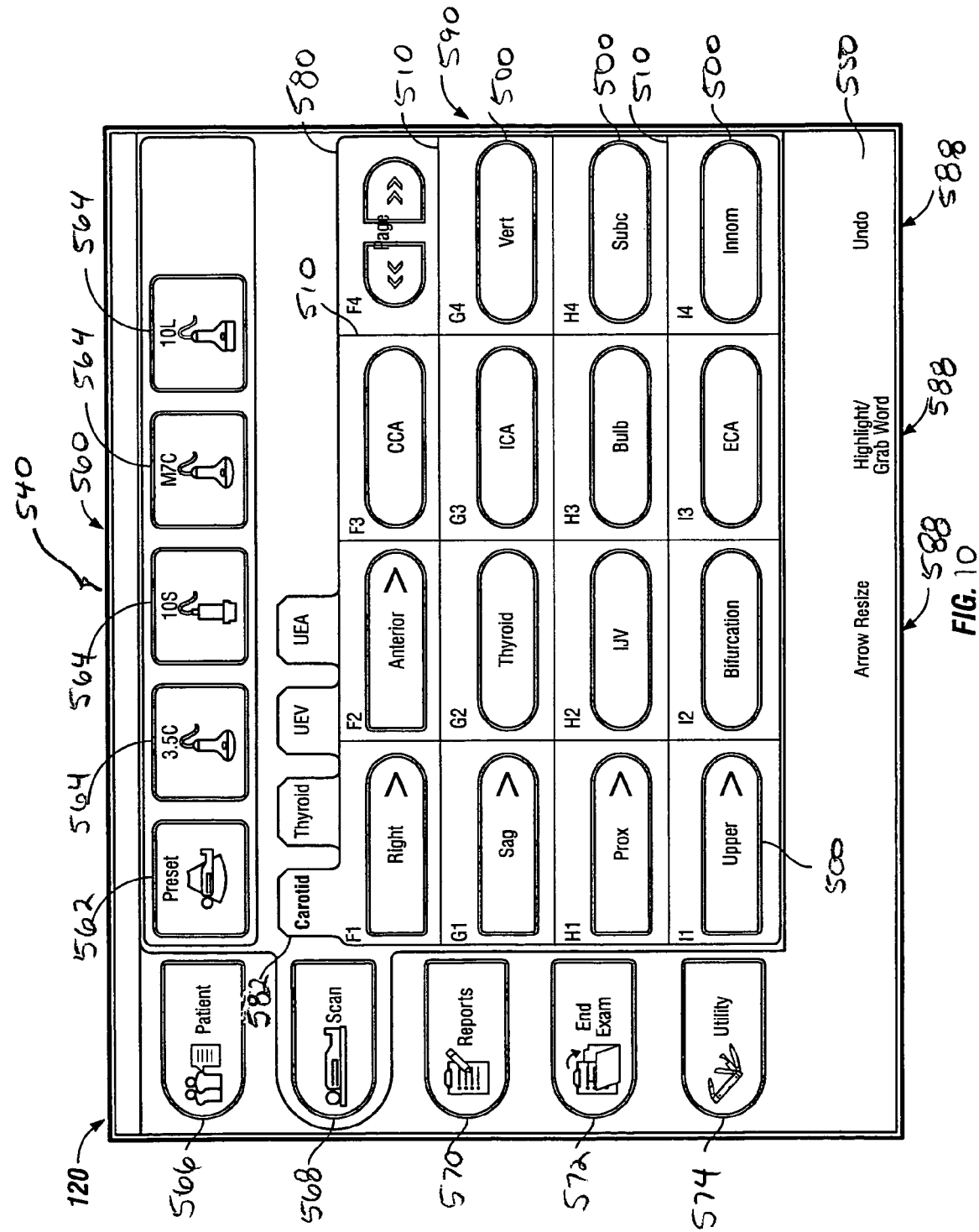
FIG. 10 is the user input of FIG. 9 displaying another exemplary control screen.

It should be noted that the number and type of icons 500 change based upon the mode of operation selected. For example, as shown in FIG. 10, the icons 500 in the control portion 580 correspond to control functionally desired or needed during a Carotid mode of operation, with the mode of operation selected and indicated by the tab 582. More than one tab 582 may be displayed on the screen 550 that are selectable by a user to change the mode of operation, thereby changing the icons 500 displayed within the control portion 580. For example, in addition to the Carotid tab 582, tabs 584 for other modes of operation, such as, Thyroid, UEV and UEA may be provided. The tabs 582 and 584 may be selected by a user or predetermined based upon a particular procedure to be performed. Thus, the tabs 582 and 584 are selectable based upon the mode of operation.

A set of indicators 588 are also provided on the screen 550 that correspond to physical controls (not shown) of the ultrasound systems 10, 100 and 200. The set of indicators 588 also change based upon the mode of operation and may, for example, indicate the level of a particular setting selectable by a physical rotary control (e.g., dynamic range as shown in FIG. 9), or the option selectable by a physical button (e.g., Undo as shown in FIG. 10). In an exemplary embodiment, each of the indicators 588 is displayed on the screen in proximity to (e.g., above) its corresponding physical control provided as part of the ultrasound systems 10, 100 and 200.

The rotaries may be labeled on touch screen 550 but not controlled by touch. Generic voice commands, "Rotary 1" and "Rotary 2" for example may be used to control such physical rotaries. For example, a voice command such as "Rotary 1 down 2" would decrease the "Power Output" setting by 2 steps for example. In other words, this voice command would cause the same effect as turning the physical rotary 2 clicks to the left. A voice command such as "Push Rotary 1" for example would cause the system to take the same action as if that physical control was pushed. Again, it is contemplated that the controls associated with the rotary 588 may change, depending on the application or system state.

In an exemplary embodiment, the control portion 580 is configured as a matrix or grid defined by grid lines 510. The matrix or grid defines locations for each of the icons 500. Specifically, an identifier 512 is associated with each grid position or cell 514 having a corresponding icon 500 therein. In an exemplary embodiment, the identifier associates a voice command with a control command represented by the icon 500 for controlling an operation or parameter of the ultrasound systems 10, 100 and 200. The identifier 512 does not change when the mode of operation changes. As described above, the icons 500 displayed in the control portion 580 may change with a change in the mode of operation. Thus, in different modes of operation, particular identifiers 512 correspond to different icons 500 for controlling a different operation or parameter during that mode of operation. It should be noted that some of the cells 514 may not include a corresponding icon 500 in a particular mode of operation.

In an exemplary embodiment, an icon is selectable by a user by touching the icon displayed on the screen 550 or by voice command. Specifically, during a particular mode of operation, a user may touch the icon 500 to select or adjust a particular parameter in that mode of operation. The various parameters or controls represented by the icons also may be selected using voice commands. In an exemplary embodiment, a user, using a voice control input, such as, for example, a microphone 530 (shown in FIGS. 3 and 4) that may be wireless or hardwired to the user input 120, may control with voice commands the operation of the ultrasound systems 10, 100 and 200. Specifically, the icons 500 may be selected using the identifier 512 associated with a particular desired or required operation or parameter. For example, the user may speak into the microphone 530 the identifier(s) 512 associated with the icon(s) 500 representing the desired or required operation or parameter, which may include a desired or required change. For example, a user may speak "G1 down," which would decrement the parameter associated with the icon in the cell 514 associated with the G1 identifier 512. Thus, a user can control the ultrasound systems 10, 100 and 200 with a simple set of voice commands defined by the identifiers 512.

It should be noted that voice commands also may be provided using word commands for operations or parameters that are often used (i.e., high use controls). For example, a user may speak "scan" to activate the scan operation associated with the Scan icon 168. The word commands may also be used in connection with high use controls in the control portion 180. Further, as should be appreciated, the voice control operation and display of icons on the screen 150 may be provided in various different manners based upon the requirements of the specific ultrasound system.

As illustrated in FIG. 10, the voice command "G2" for example would cause the Thyroid feature to be anointed as if the Thyroid key had been touched on the display, while the command "H3" for example would cause the Bulb feature to be anointed as if the Bulb key had been touched on the display. The voice command "I4" for example, would anoint the Innom feature as if the Innom key had been touched on the display. Successive commands are also contemplated in which two or more successive commands are associated with each other. In at least one embodiment, the first command would include the grid label or coordinate associate with a control, the one or more successive commands would further affect that control. This association may remain in place for a predetermined amount of time or remain in place until a different grid label or coordinate is selected, at which point that control is assumed for successive commands. Examples of voice commands including incremental values are provided in Table 1 below. However, other voice commands, which do not include incremental values are contemplated.

| Spoken Command | Action |
| --- | --- |
| I4 | Increases the control associated with grid label I4 by one (default value). So if the associated control is currently at 6, it would become 7. |
| I4 UP | Increases the control associated with grid label I4 by one (default value). It is contemplated that the defaulting be any value (5 for example.) |
| I4 UP 2 | Increases the control associated with grid label I4 by two. So if the control is currently at 3, it would become 5. |
| I4 DOWN | Decreases the control associated with grid label I4 down by one (default value). |
| I4 DOWN 2 | Decreases the control associated with grid label I4 by two. |
| I4 UP 2/UP 1 | Successive commands - First command increases the control associated with grid label 4 by two. The second command is associated with the first command, so the system changes the control associated with I4 by 1. This associated |
| ROTARY 1 | Increases the control associated with the Rotary 1 by one (default value). |
| ROTARY 1 DOWN 2 | Decreases the control associated with the Rotary 1 by two |

Although it is contemplated that values may be absolute numbers, these values are usually relative to the current value (i.e., alternatively referred to as a relative value, change value, incremental value or exact value), and represent a similar quantity (or change) that may be realized from keyboard operation. In other words, changing a value by 1 is the same as flipping the keyboard switch once or rotating a dial one click. The positive direction normally refers to flipping a switch up, right or turning a rotary clockwise. Embodiments may include commands normally handled by moving a trackball, rotary or other positioning device, including positioning and sizing a region of interest ("ROI") or moving a cursor on a display screen. In this embodiment, it is contemplated that the direction must be specified as horizontal or vertical.

During normal usage, it is contemplated that embodiments provide feedback to the user regarding what has been done. For example, after issuing a voice command, the operator may not be certain if the system heard the issued command and interpreted the command correctly. To satisfy this need, embodiments provide a non-verbal audio confirmation to the user when it hears a command (beeps/dings for example). This provides the user the opportunity to verify that the system heard the command, or to determine what the system did in case the command was misunderstood.

Figure 11:
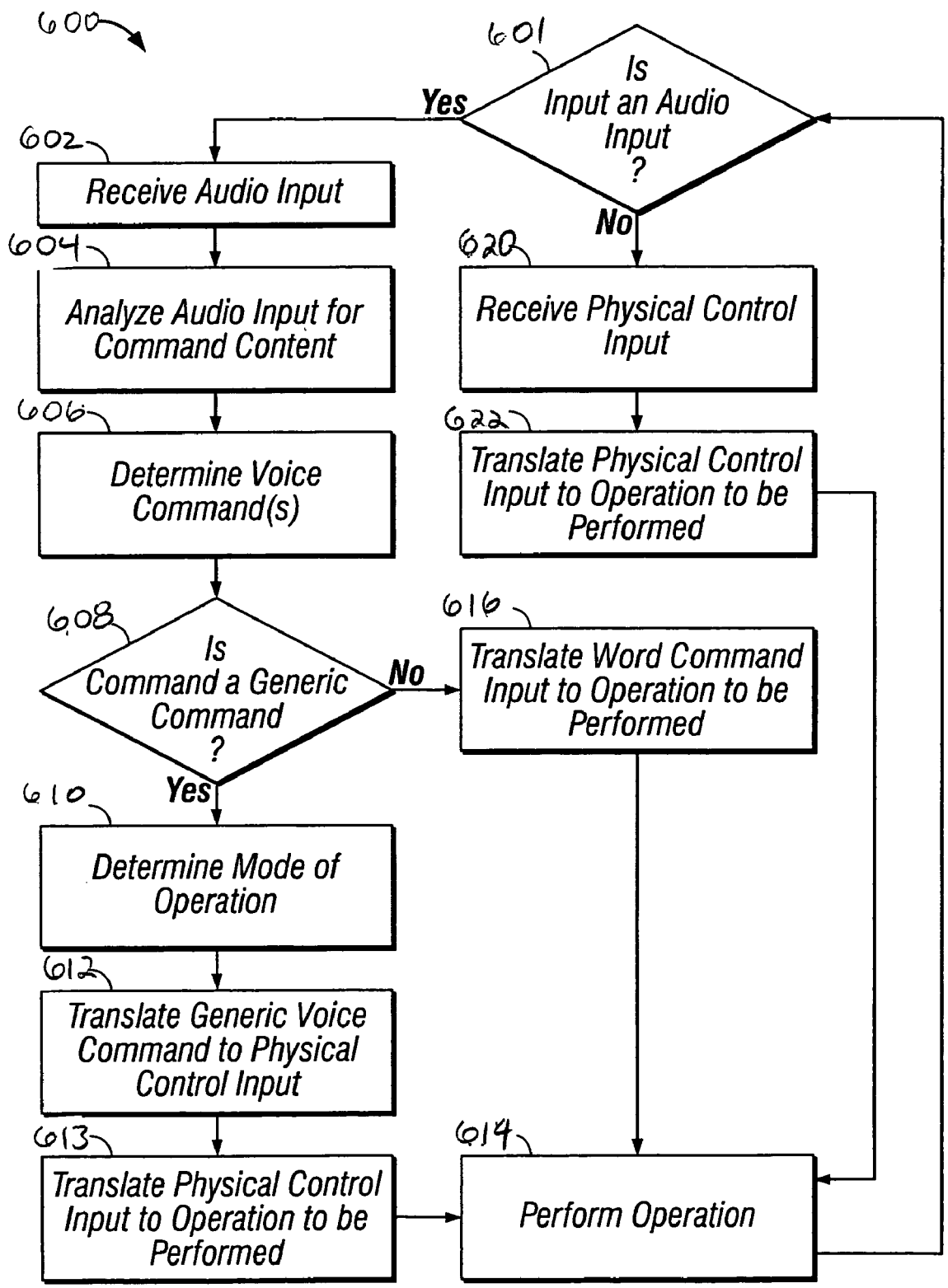
FIG. 11 is a flowchart illustrating a voice recognition process in accordance with an exemplary embodiment of the present invention.

In operation, the voice command recognition system 300 and 400 associates a voice command with a control command represented by the icon 500 for controlling an operation or parameter of the ultrasound systems 10, 100 and 200. Specifically, an exemplary embodiment of a voice recognition process 600 performed by the voice command recognition system 600 is shown in FIG. 11. At step 601, a determination is made as to whether the input to the ultrasound system 10 or 100 is an audio input. If the input is an audio input, then at step 602, an audio input (e.g., spoken words from a user) is received. The audio input is then analyzed at step 604 for command content. Based upon the analysis, recognized voice commands are determined at step 606. A determination is then made at step 608 whether the voice command(s) is a generic voice command (i.e., identifier 512). If a determination is made at step 608 that the voice command is a generic voice command, then at step 610 a determination is made as to the mode of operation of the ultrasound systems 10 or 100. At step 612, the generic voice command is translated to a physical control input. For example, using the lookup table 610 (shown in FIG. 8), the address in the database 604 (shown in FIG. 6) of the physical control input (e.g., control command) associated with the identifier 512 for the determined mode of operation is determined. Then, at step 613, the physical control input is translated to the operation to be performed (e.g., determine operation to be performed based upon the physical control input using the lookup table 810). The operation (e.g., adjustment to an operating parameter) is then performed at step 614 based upon the translated generic voice command. Another input is then processed or may be processed in parallel using the voice recognition process 600.

If a determination is made at step 608 that the voice command is not a generic voice command (e.g., command is a word command), then at step 616 the word command is translated to the operation to be performed. For example, a determination is made using the lookup table 810 as to the operation to be performed associated with any word commands (i.e., address in the database 304 (shown in FIG. 6) of the operation to be performed associated with the word command). The operation is then performed at step 614 based upon the determined address. Another input is then processed or may be processed in parallel using the voice recognition process 600.

If a determination is made at step 601 that the input to the ultrasound system 10 or 100 is not an audio input (e.g., input is a physical control input such as a change in a physical dial or switch, or touch on a touch panel) then at step 620 a physical control input (e.g., flipping a switch or rotating a rotary dial) is received. At step 622 the physical control input is translated to the operation to be performed. For example, a determination is made using the lookup table 810 as to the operation to be performed associated with the physical control input (i.e., address in the database 304 (shown in FIG. 6) of the operation to be performed associated with the physical control input). The operation is then performed at step 614 based upon the determined address. Another input is then processed or may be processed in parallel using the voice recognition process 600.

Thus, in operation, user manual action and/or voice commands may be used to control the operation of the ultrasound systems 10, 100 and 200. With respect to voice commands, and for example, using the identifiers 512, the various operations and parameters within each of the modes of operation may be easily controlled. As shown in FIGS. 9 and 10, the screen 550 includes a control portion 580 selectable by a tab 582, with each tab 582 corresponding to a grid layout representing commands and/or parameters for the selected mode of operation. A user, for example, may then speak "Tab" to select the particular tab 182 corresponding to a mode of operation, in this B-mode case, the user would speak "Tab 1", and thereafter, speak a command such as "H1" to operate a particular control within the grid, in this case to turn on/off the Compound feature as determined using the voice recognition process 400. As further examples, the voice command "I4" or "I4 Up" would increase the Line Density setting by one step. The voice command "I4 Down 2" would decrease the Line Density setting by two steps. Further, and as shown in FIG. 10, a voice command such as "Tab 2" could be used to switch from the Carotid tab to the Thyroid tab, causing the screen 550 to display a new set of icons 500 in the control portion 180.

It should be noted that the voice commands for some operations and parameters, such as low use controls, may only be operable using the generic voice commands (i.e., identifiers 512), while voice commands for some operations and parameters, such as high use commands, may be operable using the generic voice command or a word command. For example, a voice command such as "Compound" turns on/off the compounding when in the B-mode of operation as shown in FIG. 4. Alternatively, a voice command such as "H1" may also be used to turn on/off the compounding operation.

To control the physical controls (e.g., rotaries) corresponding to the set of indicators 188, and referring to FIG. 9, a voice command such as "Rotary 1 down 2" decreases the Power Output setting by two steps. It this case, the command would cause the same effect as the physical rotary being turned two clicks to the left. A voice command such as "Push Rotary 1" causes the ultrasound systems 10, 100 and 200 to take the same action as if that physical control was pushed.

Thus, the ease of use of the voice commands of the various embodiments of the present invention provides improved recognition accuracy as a result of the reduced command set size, and also decreases misinterpreted commands due to similar voice commands. Users also are not required to learn a large set of voice commands to control operation of the ultrasound machines 10, 100 and 200, for example, learning all voice commands including low use commands. Users also may view the specific generic commands on the screen 550 as needed and new or additional controls may be associated with a generic voice command (i.e., identifier 512).

Figure 12:
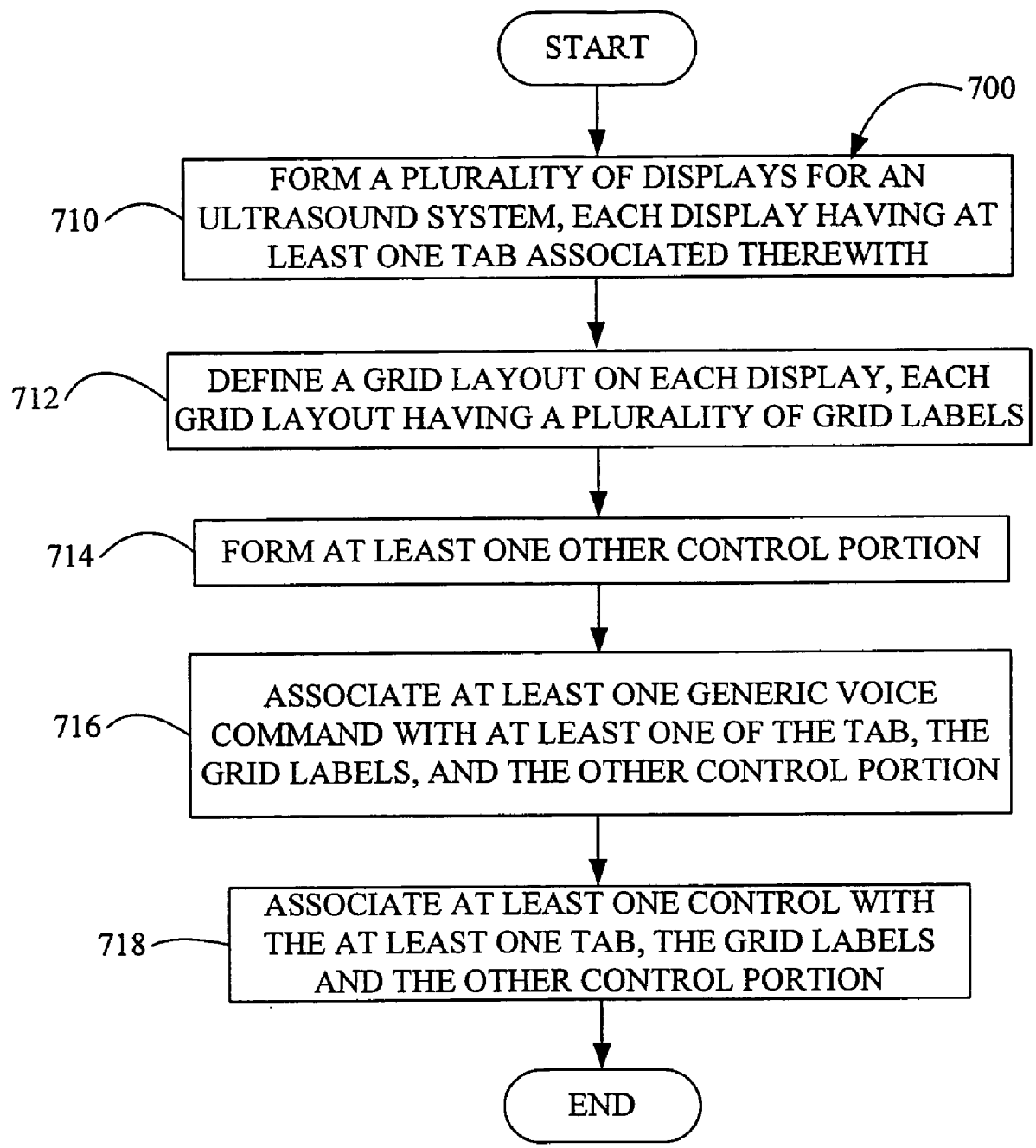
FIG. 12 is a flowchart illustrating a method for forming a generic input device or user interface responsive to voice commands used in an ultrasound system in accordance with an exemplary embodiment of the present invention.

FIG. 12 illustrates a high level flow diagram depicting a method, generally designated 700 for forming a generic input device or user interface responsive to voice commands used in an ultrasound machine, system or device in accordance with certain embodiments. In the illustrated embodiment, method 700 comprises step 700, forming at least one display for an ultrasound system, the display having at least one tab associated therewith. In at least one embodiment, step 700 comprises a plurality of displays. Method 700 further comprises step 712, defining a grid layout on the display, the grid layout having at least one grid label. In at least one embodiment, step 712 comprises each display having at least one tab, each grid layout having a plurality of grid labels.

Method 700 further comprises step 714, forming at least one third control or other control portion. In at least one embodiment, step 714 comprising a plurality of other control portions. Step 718 comprises associating at least one generic voice command with at least one of the tabs, the grid labels and the other control portion. Step 716 comprises associating at least one control with at least the one tab, the grid labels and the third control or other control portion.

Figure 13:
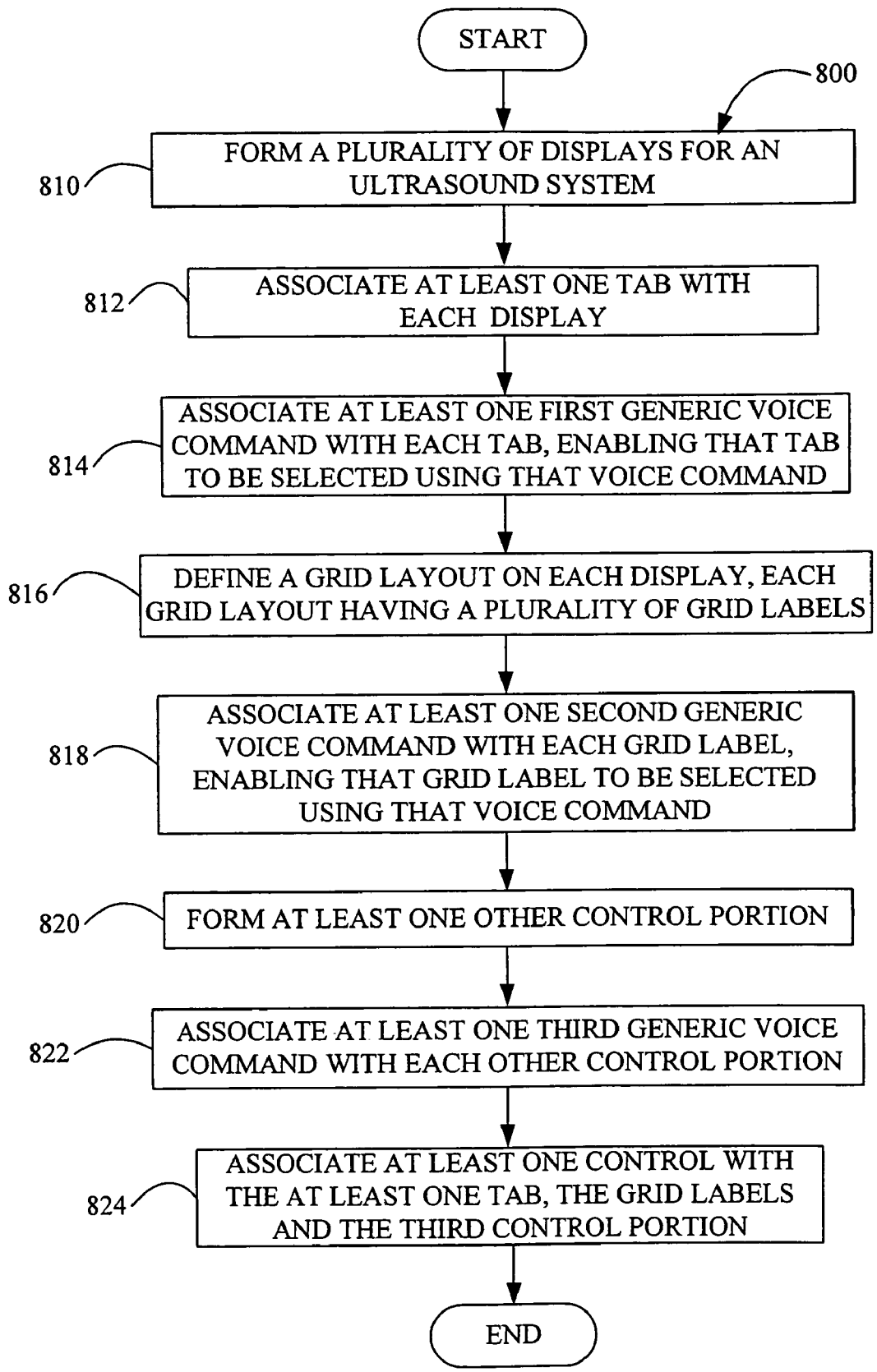
FIG. 13 is a flowchart illustrating a method for forming a generic input device or user interface responsive to voice commands used in an ultrasound system in accordance with an exemplary embodiment of the present invention.

FIG. 13 illustrates a detailed flow diagram depicting a method, generally designating 800 for forming a generic input device or user interface for controlling ultrasound system (similar to that illustrated in FIG. 1) and responsive to voice commands in accordance with certain embodiments. In the illustrated embodiment, method 800 comprises step 810, forming a plurality of displays for the ultrasound system. Step 812 comprises associating at least one tab with each of the displays. Step 814 comprises associating at least one first generic voice command with each tab, enabling that tab to be selected using that specific voice command.

Method 800 further comprises step 816, defining a grid layout on each display. In at least one embodiment, each grid layout has a plurality of grid labels. Step 818 comprises associating at least one second generic voice command with each grid label, enabling that grid label to be selected using that specific voice command. Method 800 further comprises step 820, forming at least one other control portion. Step 822 comprises associating at least one third generic voice command with each third or other control portion. Step 823 comprises associating at least one control with at least one tab, the grid layout and the other control portion. In at least one embodiment, at least one control is associated with the tab, each grid label in the grid layout and the other control portion.

Figure 14A:
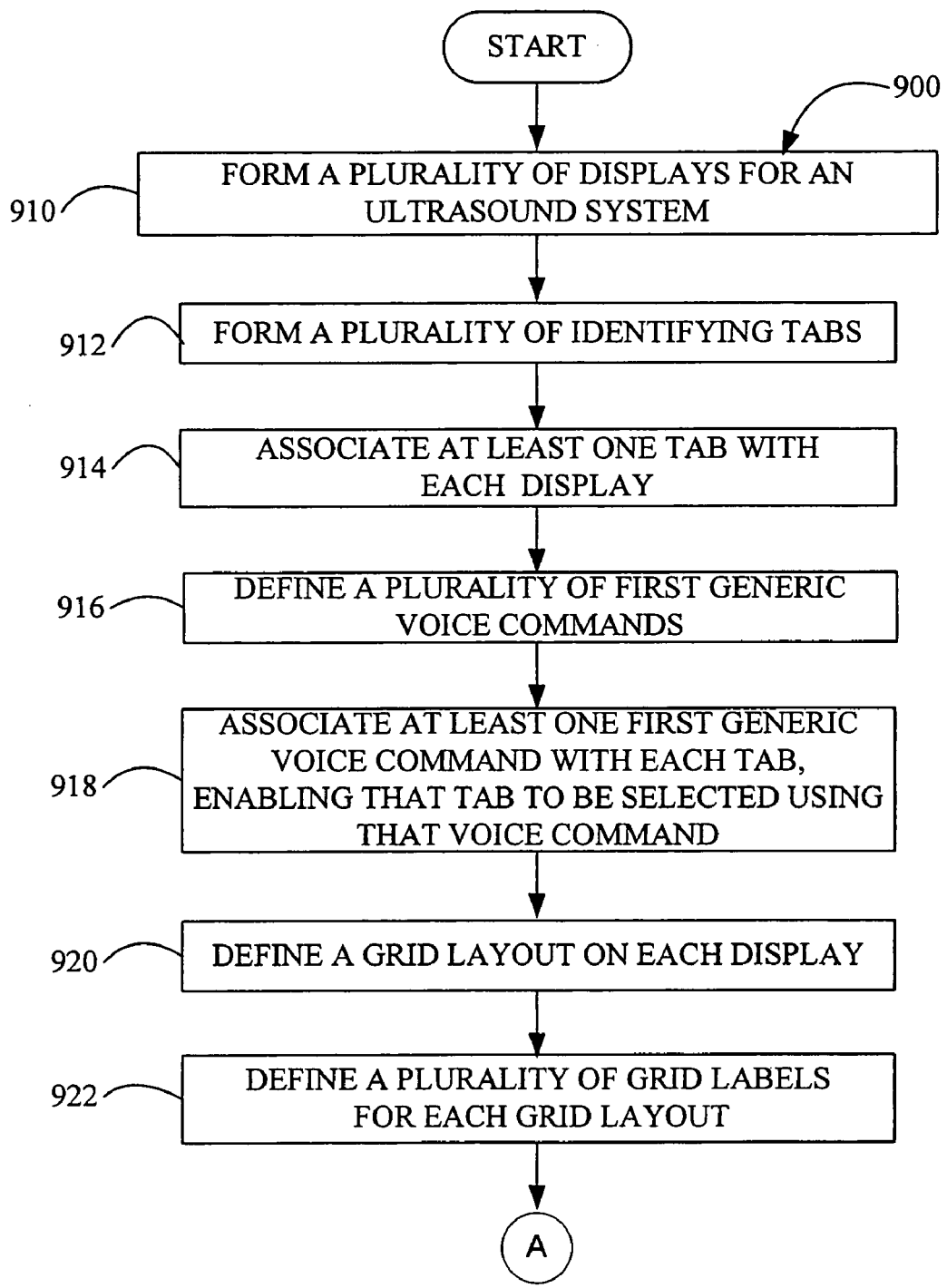
FIGS. 14A and 14B illustrate a flowchart illustrating a method for forming an input device or user interface responsive to voice commands used in an ultrasound system, such input device formed using a generic input device in accordance with an exemplary embodiment of the present invention.

FIGS. 14A and 12B illustrate a detailed flow diagram depicting a method, generally designated 900 for forming an input device or user interface responsive to one or more voice commands and used with an ultrasound system in accordance with certain embodiments. In the illustrated embodiment, method 900 comprises step 910, forming a plurality of displays in the ultrasound system. Step 912 comprises forming a plurality of identifying tabs. Step 914 comprises associating at least one tab with each of the displays.

Figure 14B:
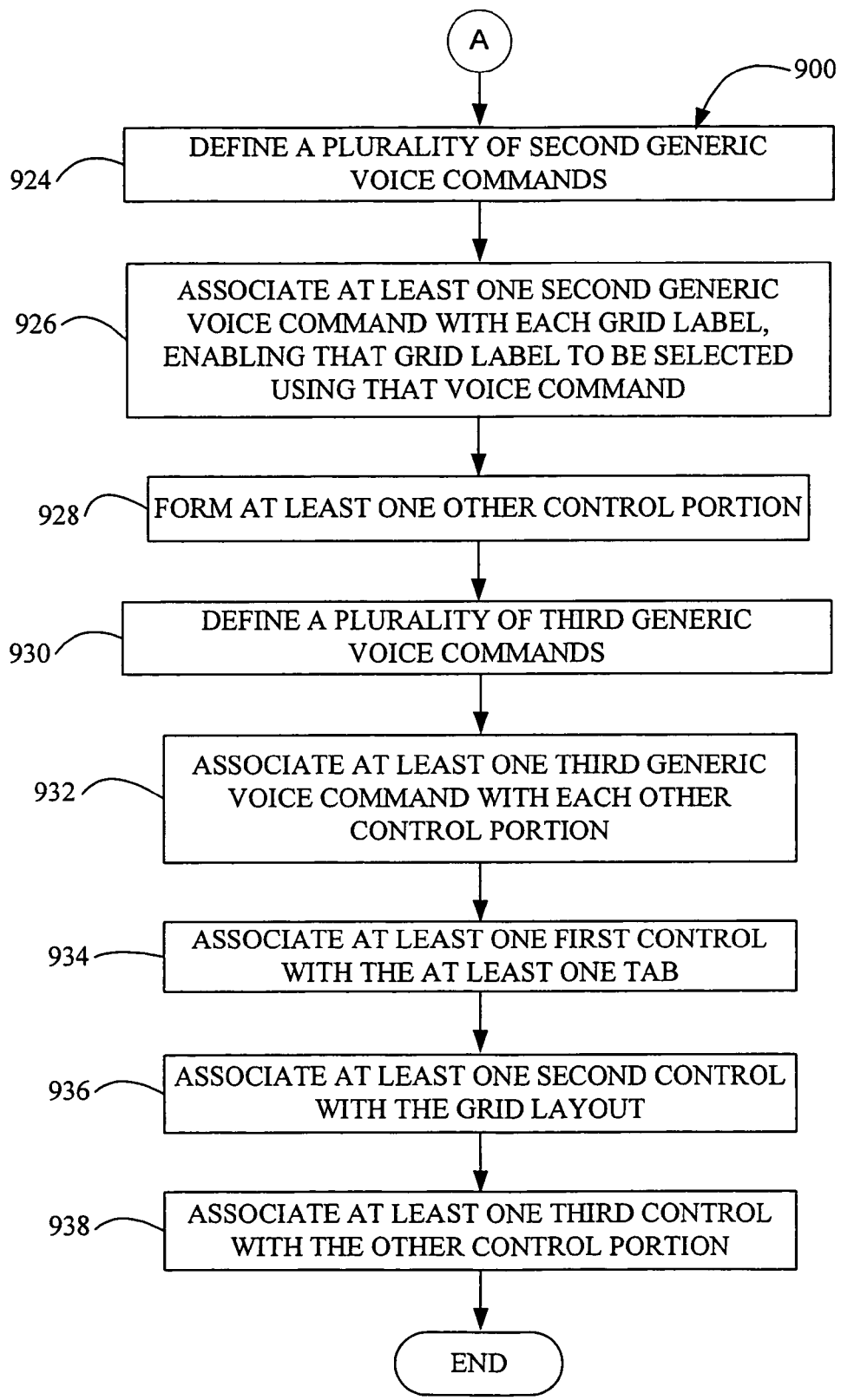

Method 900 further comprises step 916, defining a plurality of first generic voice commands. Step 918 comprises associating at least one first generic voice command with each tab, enabling that tab to be selected using that specific voice command. FIGS. 14A and 14B further illustrate step 920, defining a grid layout on each display. Step 922 comprises defining a plurality of grid labels or coordinates for each grid layout. Step 924 comprises defining a plurality of second generic voice commands. Step 926 comprises associating at least one second generic voice command with each grid label, enabling that grid label to be selected using that specific voice command.

Method 900 further comprises step 928, forming at least one other control portion and step 920, defining a plurality of third generic voice commands. Step 932 comprises associating at least one-third generic voice command with each other control portion. FIGS. 14A and 14B further comprise associating controls with the input device. In at least one embodiment, step 934 comprises associating at least one first control with the at least one tab. Step 936 comprises associating at least one second control with the grid layout. In at least one embodiment, at least one second control is associated with at least one grid label. Step 938 comprises associating at least one third control with the other control portion.

Figure 15:
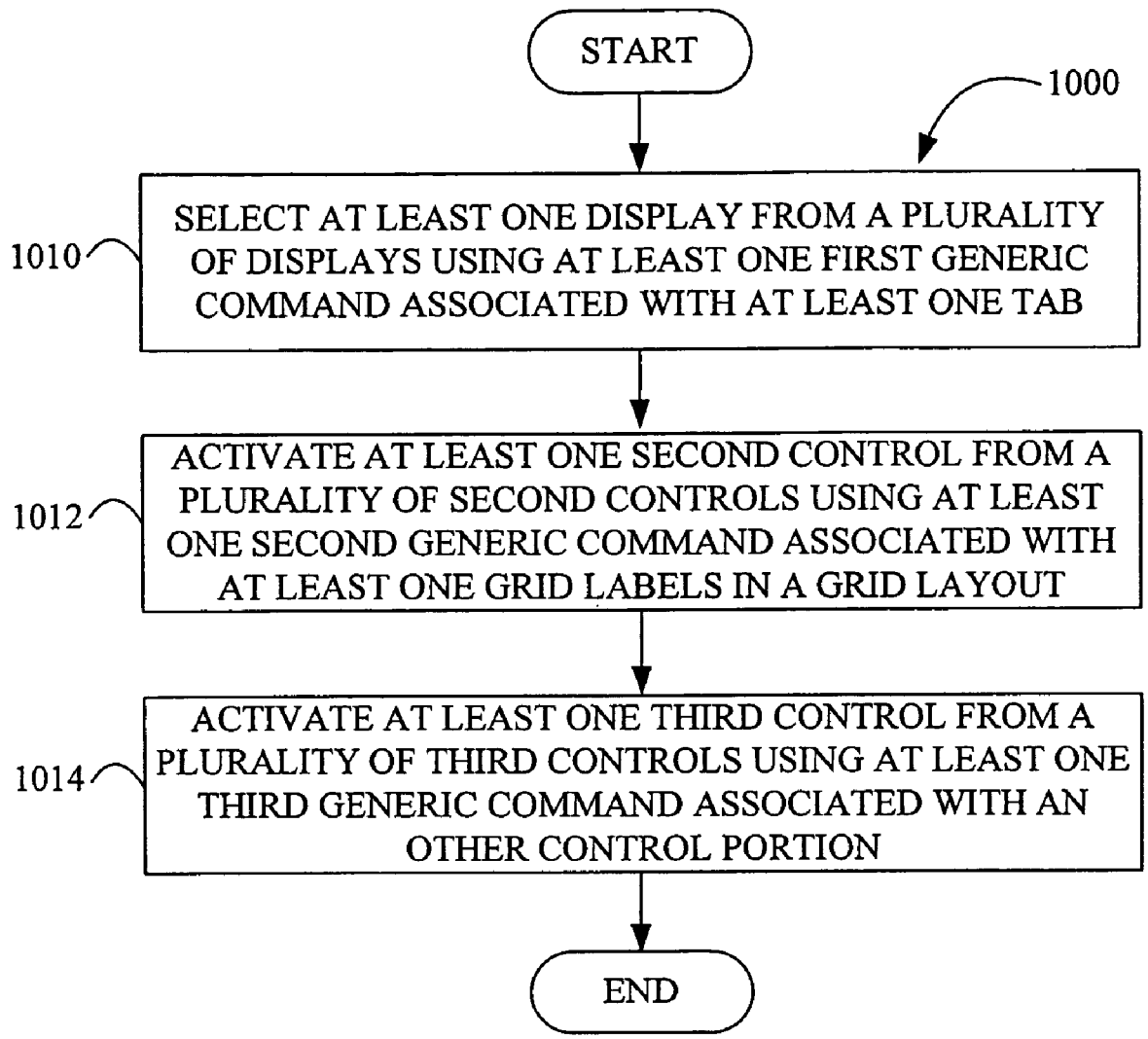
FIG. 15 is a flowchart illustrating a method of controlling an ultrasound system using an input device or user interface responsive to voice commands, such input device formed using a generic input device in accordance with an exemplary embodiment of the present invention.

FIG. 15 illustrates a flow diagram depicting a method generally designated 1000, of controlling an ultrasound system using an input device responsive to voice commands. Such input device is formed using a generic input device in accordance with certain embodiments. In the illustrated embodiment, method 1000 comprises step 1010, selecting at least one display from a plurality of displays using at least one first generic voice command. In other words, the system receives at least one voice command.

Step 1012 comprises actuating at least one second control from a plurality of second controls. The second control is selected using at least one second generic voice command. In at least one embodiment, a plurality of second generic voice commands are contemplated, where at least one second generic voice command is associated with each grid label in a grid layout. Method 1000 further comprises step 1014, actuating at least one third or other control from a plurality of third or other controls. The third control is actuated using at least one third generic voice command selected from a plurality of third generic voice commands, where at least one third voice command is associated with each third or other control.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of controlling an imaging system, comprising:
   associating a display with a tab;
   defining a grid layout on the display, wherein the grid layout is linked to the tab and comprises a matrix having a plurality of columns and rows defining cells;
   assigning identifiers and labels to each of the cells, wherein each of the identifiers and labels is assigned to one of the cells, wherein each of the identifiers consists of a letter and a number;
   associating distinct controls of the ultrasound system with the cells, wherein each of the plurality of distinct controls is associated with one of the cells; and
   associating distinct voice commands with one or both of each of the identifiers and/or labels, wherein each of the distinct controls is activated through an associated distinct voice command.

2. The method of claim 1, comprising associating a plurality of displays with a plurality of tabs, wherein each of said plurality of displays is associated with one of said plurality of tabs.

3. The method of claim 1, comprising defining a plurality of grid layouts to be displayed, wherein each of said plurality of grid layouts is linked to a particular tab.

4. The method of claim 1, wherein each of the labels comprises a description of a control.

5. A system comprising:
   an imaging device;
   a processing unit;
   a microphone operatively connected to said processing unit;
   a monitor operatively connected to said processing unit and said imaging device, said processing unit displaying a grid layout on said monitor, said grid layout being linked to a tab and comprising a matrix having a plurality of columns and rows defining cells, wherein identifiers are assigned to each of said cells, wherein each of the identifiers consists of a letter and a number, wherein unique labels are also assigned to each of said cells, said unique labels comprises a description of a control, wherein distinct controls of said imaging device are associated with each of said cells, wherein each of the labels comprises a description of a control, and wherein distinct voice commands are associated with each of said identifiers, wherein said microphone receives said distinct voice commands and said processing unit controls said imaging device through said distinct voice commands.

6. The system of claim 5, wherein said imaging device is an ultrasound imaging device comprising a transmitter, a receiver and a beamformer.

7. The system of claim 5, wherein said processor defines a plurality of grid layouts to be displayed, wherein each of said plurality of grid layouts is linked to a particular tab.

8. The system of claim 5, comprising a user input operatively connected to said processor, said user input allowing a user to enter control commands.

9. The system of claim 8, wherein said user input comprises a touch screen.

* * * * *